United States Patent
Chewter et al.

(10) Patent No.: US 9,221,726 B2
(45) Date of Patent: Dec. 29, 2015

(54) INTEGRATED PROCESS FOR THE PREPARATION OF AN AROMATIC PRODUCT

(71) Applicant: SHELL OIL COMPANY, Houston, TX (US)

(72) Inventors: Leslie Andrew Chewter, Amsterdam (NL); Sivakumar Sadasivan Vijayakumari, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 95 days.

(21) Appl. No.: 13/727,778

(22) Filed: Dec. 27, 2012

(65) Prior Publication Data

US 2013/0165716 A1   Jun. 27, 2013

(30) Foreign Application Priority Data

Dec. 27, 2011   (EP) .................................... 11195829

(51) Int. Cl.
*C07C 2/66* (2006.01)
*C07C 2/86* (2006.01)
*C07C 4/06* (2006.01)

(52) U.S. Cl.
CPC . *C07C 2/66* (2013.01); *C07C 2/864* (2013.01); *C07C 4/06* (2013.01); *C07C 2529/40* (2013.01); *C07C 2529/70* (2013.01)

(58) Field of Classification Search
USPC ................ 585/302–304, 408, 439, 437, 469, 585/638–671; 208/78–80
See application file for complete search history.

(56) References Cited

U.S. PATENT DOCUMENTS

| | | | |
|---|---|---|---|
| 4,499,314 A * | 2/1985 | Seddon et al. ................ 585/408 |
| 5,827,422 A * | 10/1998 | Drake et al. .................. 208/135 |
| 6,797,851 B2 * | 9/2004 | Martens .................... C07C 1/20 585/639 |
| 6,809,227 B2 | 10/2004 | Vaughn | |
| 2004/0102667 A1 | 5/2004 | Vora et al. | |
| 2005/0038304 A1 | 2/2005 | Van Egmond et al. | |
| 2006/0020155 A1 | 1/2006 | Beech, Jr. et al. | |
| 2008/0161620 A1* | 7/2008 | Bozzano et al. ............. 585/449 |
| 2009/0187058 A1 | 7/2009 | Chewter et al. | |
| 2010/0206771 A1 | 8/2010 | Rothaemel et al. | |
| 2010/0261943 A1 | 10/2010 | Van Westrenen et al. | |
| 2010/0268007 A1 | 10/2010 | Van Westrenen et al. | |
| 2010/0268009 A1 | 10/2010 | Van Westrenen et al. | |
| 2010/0298619 A1 | 11/2010 | Chewter et al. | |
| 2011/0009682 A1 | 1/2011 | Matsushita et al. | |
| 2011/0112344 A1 | 5/2011 | Chewter et al. | |
| 2011/0160509 A1 | 6/2011 | Van Westrenen et al. | |

* cited by examiner

*Primary Examiner* — In Suk Bullock
*Assistant Examiner* — Sharon Pregler

(57) ABSTRACT

A process preparing an aromatic product comprising xylene, the process comprising: a) cracking a feedstock to obtain a cracker effluent comprising olefins and aromatics; b) converting an oxygenate feedstock in an oxygenate-to-olefins conversion system, comprising a reaction zone in which an oxygenate feedstock is contacted with a catalyst to obtain a conversion effluent comprising benzene, toluene, xylene and olefins; c) combining at least part of the cracker effluent and at least part of the conversion effluent to obtain a combined effluent, the combined effluent comprising aromatics; d) separating at least a portion of the benzene and/or toluene from the combined effluent to form a benzene and/or toluene stream; e) separating the olefins from the combined effluent; f) separating xylene from the combined effluent to form a xylene stream; and g) recycling at least a part of the benzene and/or toluene streams as recycled aromatics to step b).

15 Claims, 1 Drawing Sheet

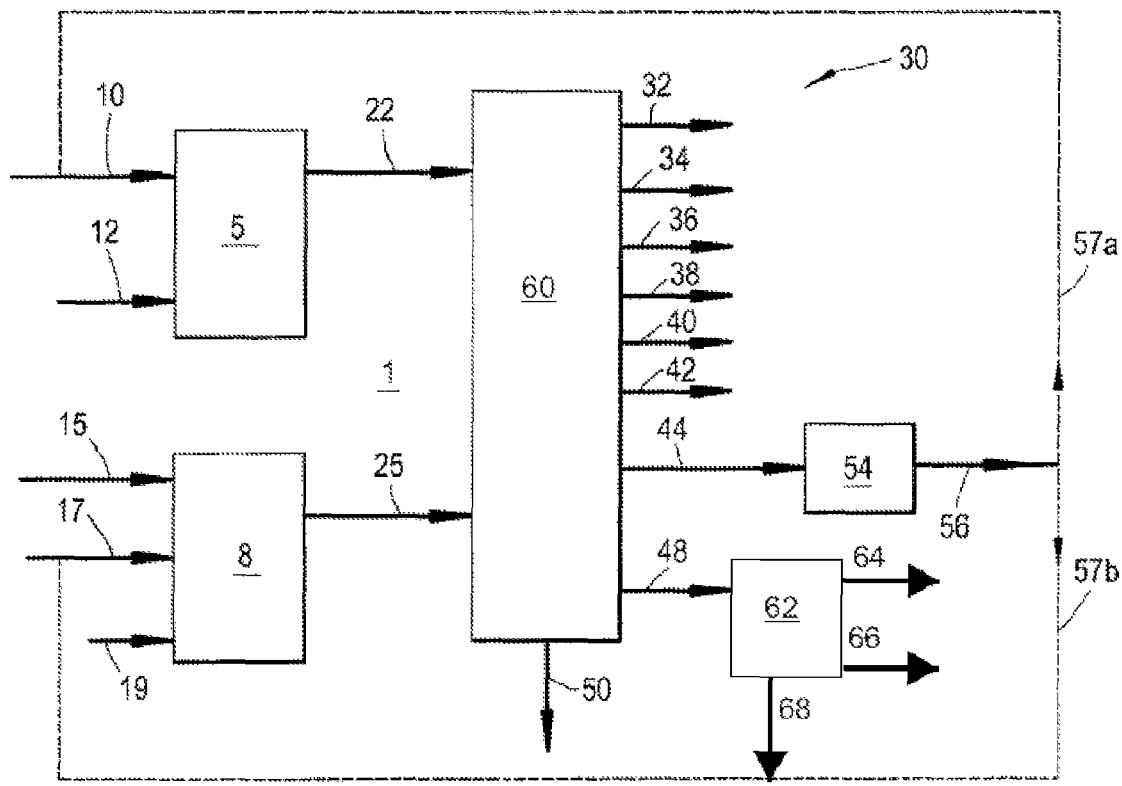

INTEGRATED PROCESS FOR THE PREPARATION OF AN AROMATIC PRODUCT

This application claims the benefit of European Patent Application No. 11195829.4, filed Dec. 27, 2011, the entire disclosure of which is hereby incorporated by reference.

FIELD OF THE INVENTION

The invention relates to an integrated process for preparing aromatics and olefins.

BACKGROUND OF THE INVENTION

Oxygenate-to-olefin processes are well described in the art. Typically, oxygenate-to-olefin processes are used to produce predominantly ethylene and propylene. An example of such an oxygenate-to-olefin process is described in US Patent Application Publication No. 2011/112344, which is herein incorporated by reference. The publication describes a process for the preparation of an olefin product comprising ethylene and/or propylene, comprising a step of converting an oxygenate feedstock in an oxygenate-to-olefins conversion system, comprising a reaction zone in which an oxygenate feedstock is contacted with an oxygenate conversion catalyst under oxygenate conversion conditions, to obtain a conversion effluent comprising ethylene and/or propylene.

The publication further describes possible integration with a cracker. The publication also describes partially hydrogenating a $C_4$ portion of the conversion effluent and/or cracker effluent and recycling at least part of the at least partially hydrogenated $C_4$ as recycle feedstock to the cracker or oxygenate-to-olefins conversion system.

While the above process is useful, it would be advantageous to produce other chemical components in an oxygenate-to-olefins process. For example, the xylene isomers are valuable chemical intermediates. Ortho-xylene can be oxidized to make phthalic anhydride which can be used to make phthalate plasticizers. Meta-xylene can be oxidized to make isophthalic acid which can be used in unsaturated polyester resins. Para-xylene can be oxidized to make terephthalic acid which is used to make polymers such as polyethylene terephthalate (PET) which is one of the largest volume polymers in the world.

SUMMARY OF THE INVENTION

The invention provides a process for the preparation of an aromatic product comprising xylene, which process comprises the steps of: a) cracking a cracker feedstock under cracking conditions in a cracking zone to obtain a cracker effluent comprising olefins and aromatics; b) converting an oxygenate feedstock in an oxygenate-to-olefins conversion system, comprising a reaction zone in which an oxygenate feedstock is contacted with an oxygenate conversion catalyst under oxygenate conversion conditions, to obtain a conversion effluent comprising benzene, toluene, xylene and olefins; c) combining at least part of the cracker effluent and at least part of the conversion effluent to obtain a combined effluent wherein the combined effluent comprises aromatics; d) separating benzene and/or toluene from the combined effluent to form a benzene and/or toluene comprising stream; e) separating xylene from the combined effluent to form a xylene stream; and f) recycling at least a part of the benzene and/or toluene comprising stream as recycled aromatics to step b).

BRIEF DESCRIPTION OF THE DRAWINGS

FIG. 1 depicts an embodiment of a process flow scheme in accordance with the invention.

DETAILED DESCRIPTION

Reference is made to FIG. 1, showing an embodiment of a process flow scheme for an oxygenate-to-olefins conversion process.

The process comprises an oxygenate-to-olefins (OTO) conversion system 8; a cracking system 5, also referred to as cracker 5; and a work-up section 60. An oxygenate feedstock is fed via line 15 to the OTO conversion system 8, for example, comprising methanol and/or dimethylether. Optionally, a hydrocarbon stream and/or a diluent are fed to the OTO conversion system via lines 17 or 19, respectively.

A cracker feedstock is fed via line 10 to the steam cracker 5. The cracker is preferably a naphtha, gas oil, hydrowax and/or vacuum gas oil cracker. Alternatively, the cracker can be a butane, propane or ethane cracker. The relative production of aromatics from the cracker is higher for naphtha and gas oil crackers which produce typically 0.7 to 0.8 tons of aromatics per ton of ethylene. Water or steam is also fed to the cracker 5 as a diluent via line 12.

In principle every known OTO conversion system and process can be used in conjunction with the present invention, including processes known as Methanol-to-Olefins (MtO) and Methanol to Propylene (MtP). The OTO conversion system and process can for example be as disclosed in US 2005/0038304, incorporated herein by reference; as disclosed in US 2010/206771, incorporated herein by reference; or as disclosed in US 2006/020155 incorporated herein by reference. Other particularly suitable OTO conversion processes and systems with specific advantages are disclosed in US 2009/187058, US 2010/298619, US 2010/268009, US 2010/268007, US 2010/261943, and US 2011/160509, all of which are herein incorporated by reference.

In one embodiment, molecular sieve catalysts are used to convert oxygenate compounds to light olefins. Silicoaluminophosphate (SAPO) molecular sieve catalyst may be used that are selective to the formation of ethylene and propylene. Preferred SAPO catalysts are SAPO-17, SAPO-18, SAPO-34, SAPO-35, SAPO-44, the substituted forms thereof and mixtures thereof. The oxygenate feedstock may comprise one or more aliphatic containing compounds, including alcohols, amines, carbonyl compounds, for example, aldehydes, ketones and carboxylic acids, ethers, halides, mercaptans, sulfides, and the like and mixtures thereof. Examples of suitable feedstocks include methanol, ethanol, methyl mercaptan, ethyl mercaptan, methyl sulfide, methyl amine, di-methyl ether, di-ethyl ether, methyl ethyl ether, methyl chloride, ethyl chloride, dimethyl ketone, formaldehyde, acetaldehyde and various acids such as acetic acid.

In one embodiment, the oxygenate feedstock comprises one or more alcohols having from 1 to 4 carbon atoms and most preferably methanol. The oxygenate feedstock is contacted with a molecular sieve catalyst and is converted to light olefins, preferably ethylene and propylene. Preferably, the OTO conversion system is arranged to receive an olefin stream and/or an aromatics stream, and is able to at least partially convert these streams to different olefins and/or aromatics. The olefin can be contacted with the oxygenate conversion catalyst in the OTO reaction zone as described in US 2009/187058, US 2010/298619 and US 2010/268009.

In another embodiment, the OTO conversion system comprises an olefin cracking zone downstream from the OTO reaction zone and is arranged to crack $C_{4+}$ olefins and/or aromatics produced in the OTO reaction zone, as described in U.S. Pat. No. 6,809,227 and US 2004/0102667. In this embodiment, at least a portion of the olefins produced in the OTO conversion are fed to the olefin cracking zone.

In one embodiment, an olefinic co-feed is fed to the oxygenate-to-olefins conversion system. An olefinic co-feed is a feed containing one or more olefins or a mixture of olefins. The olefinic co-feed may also comprise other hydrocarbon compounds, for example, paraffinic compounds, alkylaromatic compounds, aromatic compounds or mixtures thereof. The olefinic co-feed preferably comprises more than 25 wt % olefins, more preferably more than 50 wt %, still more preferably more than 80 wt % and most preferably in the range of from 95 to 100 wt % olefins. A preferred olefinic co-feed consists essentially of olefins. Non-olefinic compounds in the olefinic co-feed are preferably paraffinic compounds.

The olefins in the olefinic co-feed are preferably monoolefins. Further, the olefins can be linear, branched or cyclic, but they are preferably linear or branched. The olefins may have from 2 to 12 carbon atoms, preferably 3 to 10 carbon atoms and more preferably from 4 to 8 carbon atoms.

In one embodiment, an aromatic co-feed is fed to the oxygenate-to-olefins conversion system. An aromatic co-feed is a feed containing one or more aromatic compounds or a mixture of aromatic compounds. The aromatic co-feed may also comprise other hydrocarbon compounds, for example, paraffinic compounds, olefinic compounds or mixtures thereof. The aromatic co-feed preferably comprises more than 25 wt % aromatics, more preferably more than 50 wt %, still more preferably more than 75 wt % and most preferably in the range of from 80 to 100 wt % aromatics. A preferred aromatic co-feed consists essentially of aromatics. Non-aromatic compounds in the aromatic co-feed are preferably olefinic compounds. A preferred aromatic co-feed comprises benzene and toluene.

The aromatics can be fed to the OTO conversion system and/or to an olefin cracking unit. The aromatics may be fed alone or with olefins to either of these units. In one embodiment, the aromatics and $C_4$ stream can be fed to the OTO conversion system while a $C_5$ and $C_6$ stream is fed to an olefin cracking unit. In another embodiment, the aromatics and $C_5+$ olefins can be fed to an olefin cracking unit. In still another embodiment, a portion of the aromatics stream can be fed to the OTO conversion system and another portion of the aromatics stream can be fed to an olefin cracking unit.

Both the OTO process and the optional catalytic olefin cracking process may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

In the steam cracker 5, the cracker feedstock is cracked under cracking conditions to produce a cracker effluent comprising aromatics in line 22.

Catalysts suitable for converting the oxygenate feedstock preferably include molecular sieve-comprising catalyst compositions. Such molecular sieve-comprising catalyst compositions typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing $[TO_4]$ tetrahedral units, more preferably, two or more $[SiO_4]$, $[AlO_4]$ and/or $[PO_4]$ tetrahedral units. These silicon, aluminum and/or phosphorus based molecular sieves and metal containing silicon, aluminum and/or phosphorus based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å.

Suitable molecular sieves are silicoaluminophosphates (SAPO), such as SAPO-17, -18, 34, -35, -44, but also SAPO-5, -8, -11, -20, -31, -36, 37, -40, -41, -42, -47 and -56; aluminophosphates (AlPO) and metal substituted (silico)aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanide's of the Periodic Table of Elements, preferably Me is selected from one of the group consisting of Co, Cr, Cu, Fe, Ga, Ge, Mg, Mn, Ni, Sn, Ti, Zn and Zr.

Alternatively, the conversion of the oxygenate feedstock may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48.

Aluminosilicate-comprising catalysts, and in particular zeolite-comprising catalysts, have the additional advantage that in addition to the conversion of methanol or ethanol, these catalysts also induce the conversion of olefins to ethylene and/or propylene. Furthermore, these aluminosilicate-comprising catalysts, and in particular zeolite-comprising catalysts, are particularly suitable for use as the catalyst in a catalytic olefin cracking zone. Particular preferred catalyst for this reaction, i.e. converting part of the olefins in the olefinic product, are catalysts comprising at least one zeolite selected from MFI, MEL, TON and MTT type zeolites, more preferably at least one of ZSM-5, ZSM-11, ZSM-22 and ZSM-23 zeolites.

In one preferred embodiment, the molecular sieve in the molecular sieve-comprising catalyst is a non-zeolitic molecular sieve, while part of the olefinic product, in particular at least part of the C4+ fraction containing olefins, is provided to a subsequent separate catalytic olefin cracking zone with a zeolite-comprising catalyst and the C4+ hydrocarbon fraction is at least partially converted by contact with the zeolite-comprising catalyst.

Preferred catalysts, for both the OTO reaction as well as an optional catalytic olefin cracking reaction, comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably the channels in at least one of the directions are 10-membered ring channels. A preferred MFI-type zeolite has a Silica-to-Alumina ratio SAR of at least 60, preferably at least 80.

Particular catalysts, for both the OTO reaction as well as an optional olefin cracking reaction, include catalysts comprising one or more zeolite having one-dimensional 10-membered ring channels, i.e. one-dimensional 10-membered ring channels, which are not intersected by other channels. Preferred examples are zeolites of the MTT and/or TON type. Preferably, the catalyst comprises at least 40 wt %, preferably at least 50 wt % of such zeolites based on total zeolites in the catalyst.

In a particularly preferred embodiment the catalyst, for both the OTO reaction as well as an optional catalytic olefin cracking reaction, comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The catalyst, for both the OTO reaction as well as an optional catalytic olefin cracking reaction, may comprise phosphorus as such or in a compound, i.e. phosphorus other than any phosphorus included in the framework of the molecular sieve. It is preferred that an MEL or MFI-type zeolites comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorus as such or in a compound in an elemental amount of from 0.05-10 wt % based on the weight of the formulated catalyst. A particularly preferred catalyst comprises MEL or MFI-type zeolites having SAR of in the range of from 60 to 150, more preferably of from 80 to 100, and phosphorus, wherein the phosphorus has preferably been introduced by post-treatment of the formulated catalyst. An even more particularly preferred catalyst comprises ZSM-5 having SAR of in the range of from 60 to 150, more preferably of from 80 to 100, and phosphorus, wherein the phosphorus has preferably been introduced by post-treatment of the formulated catalyst.

It is preferred that molecular sieves in the hydrogen form are used in the oxygenate conversion catalyst in step (g), e.g., HZSM-22, HZSM-23, and HZSM-48, HZSM-5. Preferably at least 50 wt %, more preferably at least 90 wt %, still more preferably at least 95 wt % and most preferably 100 wt % of the total amount of molecular sieve used is in the hydrogen form. It is well known in the art how to produce such molecular sieves in the hydrogen form.

Typically the catalyst deactivates in the course of the process, primarily due to deposition of coke on the catalyst. Conventional catalyst regeneration techniques can be employed to remove the coke. It is not necessary to remove all the coke from the catalyst as it is believed that a small amount of residual coke may enhance the catalyst performance and additionally, it is believed that complete removal of the coke may also lead to degradation of the molecular sieve. This applies to the catalyst for both the OTO reaction as well as an optional catalytic olefin cracking reaction.

The catalyst particles used in the process of the present invention can have any shape known to the skilled person to be suitable for this purpose. The catalyst can be present in the form of spray dried catalyst particles, spheres, tablets, rings, or extrudates. Extruded catalysts can be applied in various shapes, such as, cylinders and trilobes. If desired, spent oxygenate conversion catalyst can be regenerated and recycled to the process of the invention. Spray-dried particles that are suitable for use in a fluidized bed or riser reactor system are preferred. Spherical particles are normally obtained by spray drying. Preferably the average particle size is in the range of 1-200 μm, preferably 50-100 μm.

Suitable OTO processes will be further described in detail below. In the OTO conversion system 8, the oxygenate feedstock, an aromatic stream and optionally an olefin co-feed (both of which can be partly or fully a recycle stream) are contacted with an oxygenate conversion catalyst under oxygenate conversion conditions, to obtain a conversion effluent comprising aromatics and olefins in line 25. The aromatics and/or olefins may be fed to the OTO conversion system together or separately. An optional diluent stream may comprise water, steam, inert gases such as nitrogen and/or paraffins, such as methane.

The reaction conditions of the oxygenate conversion include a reaction temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Although applicants do not wish to be bound by this theory, it is believed that the olefins fed to the OTO reactor react with the oxygenate to add additional carbon atoms, and that some of these olefins, either fed or formed in the OTO reactor are cracked into shorter chain olefins. Further, the aromatics fed to the OTO reactor react with the oxygenate to add additional carbon atoms to the aromatic. According to this theory, toluene molecules fed to the OTO reactor would be converted to xylene molecules. Further, the benzene molecules would be converted to toluene and possibly further to xylene molecules.

Alternatively, the benzene and toluene can be fed along with a $C_5$ olefin stream to an olefin cracking unit. It is believed that the benzene ring is alkylated with pentenes to form pentylbenzenes which subsequently crack into toluene and butylenes or into ethylene, propylene and benzene.

Effluents from the cracking and OTO conversion system need to be worked up in order to separate and purify various components as desired, and in particular to separate aromatic components and one or more lower olefin product streams. FIG. 1 shows a work-up section 60 which receives and processes at least part of the conversion effluent and at least part of the cracker effluent.

Typically, in known steam cracker processes as well as OTO processes, the effluent is quenched in a quench unit with a quench medium such as water to cool the process gas before feeding it to a compressor. This allows for a smaller compressor and lower power consumption due to reduced gas volume. Any liquid hydrocarbons after the quench are phase separated from liquid water and separately recovered. The water or steam recovered from the quench unit can be partially recycled as diluent to the OTO conversion system via line 19 or to the cracker via line 12. The water may first be treated or purified, for example, to remove catalyst fines or to maintain the pH at about neutral.

The vapor components after the quench are typically sent to a compression section that can comprise multiple compression steps, subjected to a caustic wash treatment, dried and sent to a separation including a cold section, to obtain separate streams of the main components. Additional compression steps may be carried out during, or after any of the above mentioned washing and drying steps. FIG. 1 shows hydrogen stream 32, light ends stream 34 typically comprising methane and/or carbon monoxide, ethane stream 36, ethylene stream 38, propane stream 40, propylene stream 42, a $C_4$ stream 44, a $C_{5+}$ stream 48 and a water effluent 50. There can also be a separate outlet for heavy (liquid) hydrocarbons. As known to one of ordinary skill in the art, the work-up section may be designed to provide different purities of each stream, and some of the streams will be produced from the work-up section as combined streams, i.e., $C_4$, $C_5$ and $C_6$ components can be combined.

It will be understood that cracker and conversion effluents can be combined at various stages of work-up, such as before quenching, after quench and before compression, or after compression.

It is advantageous to recycle at least part of the various streams to the cracker 5 and/or to the OTO conversion system 8. This invention provides an increased production of xylenes by recycling the benzene and toluene along with optional recycling of the $C_4$ and/or other olefin streams. The benzene and toluene are alkylated with the oxygenate in the OTO conversion reactor and can then be separated out as a xylene product stream. The separation of benzene and toluene from xylene may be done using general distillation methods or extractive distillation, but the separation to produce a xylene product stream is typically carried out using extractive distillation.

Some changes may be necessary to allow the system to handle the recycle of a portion of or the entire aromatics stream. For example, it is beneficial to keep the partial pressures of ethylene and propylene low in the OTO conversion system to prevent benzene and/or toluene from alkylating with the ethylene and propylene. Further, it is preferred to maintain a temperature in the range of from 575° C. to 650° C., preferably in the range of from 580° C. to 640° C. In a preferred embodiment the average temperature is about 600° C.

Further, an ethane and/or butane stream can be recycled to the cracker 5 via line 57a to produce additional olefins and/or aromatics. A $C_4$ olefin or $C_{4+}$ olefin stream may be recycled to the OTO reactor via line 57b.

Typically, both the steam cracker effluent and the OTO conversion system effluent will contain $C_4$ species, in particular including unsaturated $C_4$ species. The cracker effluent will typically contain more butadiene than the conversion effluent. The effluents from both the cracker and the OTO conversion typically also contain butene and a quantity of butane. The butadiene may be removed through selective hydrogenation as described below or by butadiene extraction.

In addition, the $C_5+$ streams may comprise diolefins and/or other undesired components such as sulfur compounds. A pyrolysis gas hydrotreatment may be required to hydrotreat these streams. The OTO catalyst is preferably resistant to poisoning by any undesired components, but alternatively, these components are removed before recycling the streams to the OTO conversion system. The pyrolysis gas hydrotreatment may comprise two hydrogenation steps and some of the olefins may be removed after the first hydrogenation step, e.g., the $C_5$ olefins; while the C6+ fraction may be completely hydrogenated in the second step.

FIG. 1 shows xylene product stream 66 being produced from the workup section. In one embodiment this is a mixed xylene stream that may be fed to a further process suitable for converting the mixed xylene stream into a para-xylene stream.

FIG. 1 shows aromatics stream 68, and a portion or this entire stream may be recycled to the OTO conversion system 8. The aromatics stream could be fed with the $C_4$ recycle via lines 57 and 17. One of ordinary skill in the art will recognize that the work-up section could be operated such that the aromatics and $C_{4+}$ streams are not separated, but fed together to the OTO conversion system, after an optional selective hydrogenation step.

In one embodiment, the $C_4$ stream may be separated and the $C_5+$ olefin stream and the aromatics are not separated. This combined aromatics and $C_5+$ olefin stream can be fed to an olefin cracking unit and/or to an OTO conversion system.

In a preferred embodiment, the $C_4$ olefin stream and the benzene and toluene are fed to the OTO conversion system, and the $C_5$ and $C_6$ olefins are fed to an olefin cracking unit.

In a preferred embodiment, the C4 olefin stream, oxygenate and toluene are fed to the OTO conversion system. As can be seen from the examples, this produces the most xylene without the production of large amounts of $C_9+$ aromatics which are not typically seen as valuable chemicals. Further, the amount of oxygenate may be restricted to prevent overalkylation of the benzene and toluene in the OTO conversion system. Alternatively, the method of feeding the oxygenate and/or the location where the oxygenate is fed into the OTO conversion system may be adjusted to prevent overalkylation of the benzene and toluene.

FIG. 1 shows the $C_4$ stream 44 being fed to a hydrogenation unit 54. All or part of the $C_4$ stream may be at least partially hydrogenated with a source of hydrogen. The at least partially dehydrogenated $C_4$ stream can be recycled to the OTO conversion system via line 57b and line 17. When recycling to the OTO, the recycle $C_4$ stream can be a co-feed to the OTO reaction zone or it can be a feed to an optional catalytic olefin cracking zone downstream from the OTO reaction zone. Suitable catalysts and conditions are described herein, as well as in U.S. Pat. No. 6,809,227 and US 2004/0102667. Catalysts include those comprising zeolitic molecular sieves such as MFI-type, e.g., ZSM-5, or MEL-type, e.g., ZSM-11, as well as Boralite-D and silicalite 2.

In one particular embodiment, the stream 44 comprises a significant quantity of di-olefins, in particular butadiene. A significant quantity of butadiene is for example, at least 0.1 wt % of butadiene in the stream, in particular at least 0.5 wt %, more in particular at least 1 wt %, or at least 2 wt %. The stream comprising a significant quantity of butadiene may be subjected to selective hydrogenation conditions in hydrogenation unit 54 to convert butadiene to butene, but preferably minimizing the hydrogenation of butene to butane. A suitable process for selective hydrogenation is described in U.S. Pat. No. 4,695,560. It is preferred for at least 90 wt % of the butadiene to be converted to butene and less than 10 wt %, preferably less than 5 wt % of the butene to be converted to butane.

The effluent from selective hydrogenation is a $C_4$ feedstock comprising butene, and butene is a desirable co-feed in OTO reactions, in particular in the MtP process or in a process in which a catalyst comprising an aluminosilicate or zeolite having one-dimensional 10-membered ring channels and an olefin co-feed is employed. The butene rich effluent can be recycled via line 57b.

An optional bleed line to remove butane and/or other saturates from the recycle line can be present in the system as these components are not typically reacted in the OTO reactor. In addition, the $C_5$ and/or $C_6$ olefin streams may be recycled to the OTO reactor and/or to an olefin cracking unit.

In another embodiment, stream 44 comprising unsaturated $C_4$ species is subjected to more severe hydrogenation conditions in unit 54 so that butenes as well as any butadiene are substantially fully hydrogenated, and an effluent rich in butane is obtained in line 56. Such a butane-rich stream can be recycled as feedstock to the steam cracker 5 via line 57a to produce additional ethylene. In another embodiment, the butadiene and/or toluene may be removed by extraction.

EXAMPLES

Example 1

Two catalysts, comprising 40 wt % zeolite, 36 wt % kaolin and 24 wt % silica were tested to show their ability to alkylate toluene to xylene and heavier aromatics. To test the catalyst formulations for catalytic performance, the catalysts were pressed into tablets and the tablets were broken into pieces and sieved.

In the preparation of the first catalyst sample ZSM-23 zeolite powder with a silica to alumina molar ratio (SAR) 46, and ZSM-5 zeolite powder with a SAR of 80 were used in the ammonium form in the weight ratio 50:50. Prior to mixing the powders, the ZSM-5 zeolite powder was treated with phosphorus, resulting in a catalyst that has only one zeolite pretreated with phosphorus. Phosphorus was deposited on a ZSM-5 zeolite powder with a silica-to-alumina ratio of 80 by means of impregnation with an acidic solution containing phosphoric acid to obtain a ZSM-5 treated zeolite powder containing 2.0 wt % P. The ZSM-5 powder was calcined at 550° C. Then, the powder mix was added to an aqueous solution and subsequently the slurry was milled. Next, kaolin clay and a silica sol were added and the resulting mixture was spray dried wherein the weight-based average particle size was between 70-90 µm. The spray dried catalysts were exposed to ion-exchange using an ammonium nitrate solution. Then, phosphorus was deposited on the catalyst by means of impregnation using acidic solutions containing phosphoric acid ($H_3PO_4$). The concentration of the solution was adjusted to impregnate 1.0 wt % of phosphorus on the catalyst. After impregnation the catalysts were dried at 140° C. and were calcined at 550° C. for 2 hours. The final formulated catalyst thus obtained is further referred to as catalyst 1.

A second catalyst was prepared as described herein above for catalyst 1, with the exception that only ZSM-5 with a SAR of 80 was used and it was not treated with phosphorus prior to spray drying. The concentration of the phosphorus impregnation solution was adjusted to impregnate 1.5 wt % of phosphorus on the catalyst formulation. The final formulated catalyst thus obtained is further referred to as catalyst 2.

The phosphorus loading on the final catalysts is given based on the weight percentage of the elemental phosphorus in any phosphor species, based on the total weight of the formulated catalyst.

Toluene in the presence of methanol was reacted over the catalysts which were tested to determine their selectivity towards heavier aromatics, mainly ortho, meta and para xylene. For the catalytic testing, a sieve fraction of 60-80 mesh was used. The reaction was performed using a quartz reactor tube of 1.8 mm internal diameter. The molecular sieve samples were heated in nitrogen to the reaction temperature and a mixture consisting of 4.3 vol % toluene, 6% vol % methanol balanced in $N_2$ was passed over the catalyst at atmospheric pressure (1 bar). The Gas Hourly Space Velocity (GHSV) is determined by the total gas flow over the zeolite weight per unit time (ml gas)/(g zeolite·hr). The gas hourly space velocity used in the experiments was 19000 (ml gas)/(g zeolite·hr). The effluent from the reactor was analyzed by gas chromatography (GC) to determine the product composition. The composition was calculated on a weight basis of all hydrocarbons analyzed. The composition was defined by the division of the mass of specific product by the sum of the masses of all products. The effluent from the reactor obtained at several reactor temperatures was analyzed. The results are shown in Table 1.

The tests were repeated with two different feeds. The second feed, for which results are shown in Table 2 comprised 3 vol % toluene, 3 vol % 1-butene and 3 vol % methanol balanced in $N_2$. The third feed, for which results are shown in Table 3 comprised 3 vol % toluene and 3 vol % 1-butene balanced in $N_2$.

The conversion of toluene varies from 82.45% to 78.58%. As can be seen from the results, higher temperature favors conversion of toluene to xylene and heavier aromatics and reduces side chain alkylation to form light ends. Additionally, some ethylene and propylene are formed as toluene alkylation takes place on the side chain to form an ethyl or propyl group, that is then broken off of the aromatic compound and forms an ethylene or propylene molecule.

When co-feeding 1-butene in the presence of toluene and methanol, toluene conversion drops to 65% with an equal drop in $C_9$ aromatics make due to the competing alkylation of the butene-1. Further, the alkylation of toluene in the absence of methanol is significantly less as shown in Table 3.

TABLE 1

| Catalyst | Temp. (° C.) | LE (wt %) | C2 (wt %) | C3 (wt %) | C4 (wt %) | C5+ (wt %) | B (wt %) | T (wt %) | X (wt %) | C9+ arom. (wt %) |
|---|---|---|---|---|---|---|---|---|---|---|
| 1 | 525 | 1.00 | 6.03 | 4.15 | 1.60 | 0.79 | 0.08 | 24.80 | 44.67 | 16.89 |
| 1 | 600 | 2.35 | 4.57 | 2.39 | 1.22 | 0.73 | 0.18 | 17.55 | 51.08 | 19.93 |
| 2 | 525 | 1.93 | 5.81 | 3.46 | 1.23 | 0.66 | 0.00 | 21.42 | 46.78 | 18.70 |
| 2 | 600 | 3.30 | 3.70 | 1.58 | 1.01 | 0.59 | 0.09 | 15.90 | 50.07 | 23.75 |

TABLE 2

| Catalyst | Temp. (° C.) | LE (wt %) | C2 (wt %) | C3 (wt %) | C4 (wt %) | C5+ (wt %) | B (wt %) | T (wt %) | X (wt %) | C9+ arom. (wt %) |
|---|---|---|---|---|---|---|---|---|---|---|
| 1 | 525 | 0.96 | 7.48 | 20.57 | 11.98 | 4.19 | 0.27 | 35.29 | 17.66 | 1.60 |
| 2 | 525 | 1.38 | 8.31 | 20.85 | 10.65 | 3.59 | 0.59 | 35.48 | 17.21 | 1.94 |
| 1 | 600 | 2.19 | 9.00 | 19.71 | 10.53 | 2.06 | 0.73 | 33.88 | 19.78 | 2.11 |
| 2 | 600 | 3.54 | 10.13 | 19.31 | 8.73 | 1.59 | 1.29 | 33.52 | 18.81 | 3.08 |

TABLE 3

| Catalyst | Temp. (° C.) | LE (wt %) | C2 (wt %) | C3 (wt %) | C4 (wt %) | C5+ (wt %) | B (wt %) | T (wt %) | X (wt %) | C9+ arom. (wt %) |
|---|---|---|---|---|---|---|---|---|---|---|
| 1 | 525 | 0.00 | 2.99 | 10.83 | 20.75 | 3.33 | 0.23 | 61.41 | 0.39 | 0.08 |
| 2 | 525 | 0.00 | 4.32 | 14.20 | 16.36 | 2.68 | 0.59 | 60.82 | 0.80 | 0.22 |

TABLE 3-continued

| Catalyst | Temp. (° C.) | LE (wt %) | C2 (wt %) | C3 (wt %) | C4 (wt %) | C5+ (wt %) | B (wt %) | T (wt %) | X (wt %) | C9+ arom. (wt %) |
|---|---|---|---|---|---|---|---|---|---|---|
| 1 | 600 | 0.03 | 3.22 | 6.64 | 24.95 | 1.60 | 0.70 | 61.72 | 0.90 | 0.24 |
| 2 | 600 | 0.54 | 5.04 | 9.70 | 19.45 | 1.53 | 1.41 | 59.76 | 1.81 | 0.76 |

What is claimed is:

1. A process for the preparation of an aromatic product comprising xylene, which process comprises the steps of:
  a. cracking a cracker feedstock under cracking conditions in a cracking zone to obtain a cracker effluent comprising olefins and aromatics;
  b. converting an oxygenate feedstock in an oxygenate-to-olefins conversion system, comprising a reaction zone in which an oxygenate feedstock is contacted with an oxygenate conversion catalyst under oxygenate conversion conditions, to obtain a conversion effluent comprising benzene, toluene, xylene and olefins, wherein the oxygenate conversion conditions comprise a temperature in the range of from 575° C. to 650° C. and a pressure in the range of from 100 kPa to 1.5 MPa;
  c. combining at least part of the cracker effluent and at least part of the conversion effluent to obtain a combined effluent wherein the combined effluent comprises aromatics;
  d. separating at least a portion of the benzene and toluene from the combined effluent;
  e. separating the olefins from the combined effluent;
  f. separating xylene from the combined effluent to form a xylene stream; and
  g. recycling at least a part of the benzene and toluene as recycled aromatics to step b).

2. A process as claimed in claim 1 wherein the oxygenate conversion catalyst comprises at least one zeolite selected from MFI, MEL, TON and MTT zeolites.

3. A process as claimed in claim 1 wherein the oxygenate conversion catalyst comprises at least one zeolite selected from ZSM-5, ZSM-11, ZSM-22 and ZSM-23 zeolites.

4. A process as claimed in claim 1 wherein the cracker feedstock comprises naphtha or gas oil.

5. A process as claimed in claim 1 wherein the cracking conditions comprise a temperature of from 650 to 1000° C.

6. A process as claimed in claim 1 wherein the oxygenate feedstock is selected from the group consisting of methanol, ethanol, tert-alkyl ethers and mixtures thereof.

7. A process as claimed in claim 1 further comprising recycling at least a portion of the olefins to step b).

8. A process as claimed in claim 1 further comprising separating a diolefin rich stream from the combined effluent and partially hydrogenating the diolefin rich stream.

9. A process as claimed in claim 1 further comprising separating an alkane rich stream from the combined effluent and recycling at least a portion of the alkane rich stream to step a).

10. A process as claimed in claim 9 wherein the alkane stream comprises butane.

11. A process for the preparation of an aromatic product comprising xylene, which process comprises the steps of:
  a. cracking a cracker feedstock under cracking conditions in a cracking zone to obtain a cracker effluent comprising olefins and aromatics;
  b. converting an oxygenate feedstock in an oxygenate-to-olefins conversion system, comprising a reaction zone in which an oxygenate feedstock is contacted with an oxygenate conversion catalyst under oxygenate conversion conditions, to obtain a conversion effluent comprising benzene, toluene, xylene and olefins, wherein the oxygenate conversion conditions comprise a temperature in the range of from 50-0G° 575° C. to 650° C. and a pressure in the range of from 100 kPa to 1.5 MPa;
  c. combining at least part of the cracker effluent and at least part of the conversion effluent to obtain a combined effluent wherein the combined effluent comprises aromatics;
  d. separating at least a portion of the benzene and toluene from the combined effluent;
  e. separating the olefins from the combined effluent;
  f. separating xylene from the combined effluent to form a xylene stream;
  g. recycling at least a part of the benzene and as recycled aromatics to step b); and
  h. feeding at least a portion of the olefins to an olefin cracking unit in which the olefins are contacted with an olefin cracking catalyst under cracking conditions, to obtain an olefin cracking effluent.

12. A process as claimed in claim 11 wherein the portion of the olefins fed to the olefin cracking unit comprises olefins having from 5 to 6 carbon atoms.

13. A process as claimed in claim 12 wherein at least 50 wt % of the portion of the olefins fed to the olefin cracking unit is olefins having from 5 to 6 carbon atoms.

14. A process as claimed in claim 11 wherein the olefin cracking effluent comprises olefins having from 2 to 3 carbon atoms.

15. A process as claimed in claim 14 wherein the olefin cracking effluent comprises at least 50 wt % of olefins having from 2 to 3 carbon atoms.

* * * * *